United States Patent [19]

Hruby

[11] Patent Number: 4,649,191

[45] Date of Patent: Mar. 10, 1987

[54] CONFORMATIONALLY CONSTRAINED ALPHA-MELANOTROPIN ANALOGS WITH SPECIFIC CENTRAL NERVOUS SYSTEM ACTIVITY

[75] Inventor: Victor J. Hruby, Tucson, Ariz.

[73] Assignee: Gibson-Stephens Neuropharmaceuticals, Inc., Tucson, Ariz.

[21] Appl. No.: 608,708

[22] Filed: May 10, 1984

[51] Int. Cl.[4] .............................................. C07K 7/06
[52] U.S. Cl. .................................................... 530/329
[58] Field of Search ................ 260/112.5 R; 424/177; 530/329

[56] References Cited

PUBLICATIONS

Knittel et al., Journal of Medicinal Chemistry, 28, 125–129 (1983).
Sawyer et al., Journal of Medicinal Chemistry, 25, 1022–1027 (1982).
Sawyer et al., Proc. Natl. Acad. Sci., USA, 79, 1751–55 (1982).
Chemical Abstracts, 101, 74 (1984), Abst. No. 66177X.
Chemical Abstracts, 97, 102 (1982), Abst. No. 17366Z.

Primary Examiner—Delbert R. Phillips

[57] ABSTRACT

Novel compounds which are analogs of α-melanotropin and which exhibit reactivity for the central nervous system receptors without exhibiting substantial reactivity for the peripheral receptors are disclosed. The compounds of the present invention are polypeptides of the formula:

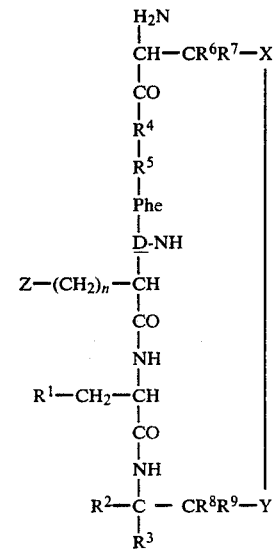

wherein
$R^1$ is a substituted or unsubstituted aromatic radical;
$R^2$ is hydrogen or a methyl group;
$R^3$ is carboxylate, carboxamide, hydroxymethyl, or aldehyde group or a peptide residue;
$R^4$ is a simple amino acid residue;
$R^5$ is a simple amino acid residue;
$R^6$ and $R^7$, which may be the same or different, are hydrogen, methyl or lower alkyl having one to five carbon atoms;
$R^8$ and $R^9$, which may be the same or different, are hydrogen, methyl or lower alkyl having one to five carbon atoms;
X and Y are sulfur, methylene, SO, or $SO_2$;
Z is $-NH_2$,

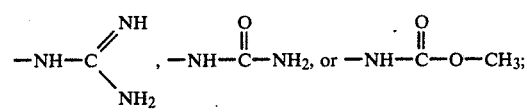

and
n is an integer greater than or equal to 2.

The noval compounds may be used in humans and lower animals to facilitate memory and behavior, improve fetal growth and development, enhance attention, improve socialization, stimulate sexual activity, reverse morphine analgesia, act as an antidepressant, act as an antipyretic and centrally direct effects on visceral functions.

12 Claims, No Drawings

CONFORMATIONALLY CONSTRAINED ALPHA-MELANOTROPIN ANALOGS WITH SPECIFIC CENTRAL NERVOUS SYSTEM ACTIVITY

This invention relates to compounds that are cyclic analogs of α-melanotropin and which exhibit a high degree of specificity for the central nervous system receptors with minimal specificity for peripheral receptors. This invention also relates to a method of inducing pharmacological manifestations associated with central nervous system specificity, such as by administering a safe and effective amount of the melanotropin compound.

BACKGROUND OF THE INVENTION

α-Melanotropin is a naturally occurring tridecapeptide which is believed to interact with numerous receptors to induce various pharmacological activities. α-Melanotropin, also known as α-MSH and α-melanocyte stimulating hormone, has the following formula: Ac-Ser$^1$-Tyr$^2$-Ser$^3$-Met$^4$-Glu$^5$-His$^6$-Phe$^7$-Arg$^8$-Trp$^9$-Gly$^{10}$-Lys$^{11}$-Pro$^{12}$-Val$^{13}$-NH$_2$ Before proceeding further, it is necessary to explain briefly the terminology used to describe polypeptides. Peptides are identified by amino acid sequence using established abbreviations. For example, as used herein, "Gly" stands for glycine, "Glu" stands for glutamic acid, "Tyr" stands for tyrosine, "Ser" stands for serine, "Met" stands for methionine, "Phe" stands for phenylalanine, "His" stands for histidine, "Arg" stands for arginine, "Trp" stands for tryptophan, "Lys" stands for lysine, "Pro" stands for proline, "Val" stands for valine, and "Cys" stands for cysteine. Polypeptide derivatives in which one or more of the amino acids have been replaced by another amino acid are often described by reference to the basic compound and the position and nature of the substitution. The position of substitution is usually identified by reference to the number of the amino acid in the sequence starting with the amino acid at the amino terminus of the peptide chain. For example,

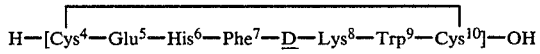

is written as

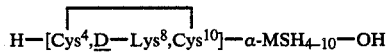

signifying that cysteine has been substituted for the methionine normally found as the fourth amino acid from the amino terminus in α-melanotropin. The 4-10 subscript in the formula indicates that the named compound includes the amino acid sequence in the 4-10 positions of naturally occurring α-MSH. Additionally, amino acids may exist as stereoisomers in both L and D configurations. Thus, for example, as used herein "D-Lys" identifies the D optical isomer of Lysine.

The mechanism of action of peptide hormones and/or neurotransmitters is believed to be via interaction with receptors. A receptor is that entity, on a cell, which recognizes and binds a chemical substance. For purposes of explaining the action of α-MSH, receptors may be separated into two broad categories: receptors on the cells found in peripheral tissue, such as the muscles, liver, kidney and skin, and receptors which are on cells of the central nervous system (hereinafter sometimes referred to as CNS) such as the brain, spinal cord and the numerous nerve fibers.

The receptor binding properties of a particular compound dictate the physiological effect that a particular compound will produce. For example, one of the effects of α-MSH is to reversibly darken the skin by stimulating melanin synthesis. Another effect of α-MSH is to stimulate melanocyte dispersion. Both of these effects are peripheral.

Melanotropin exhibits a wide variety of physiological and pharmacological activities besides skin darkening, as related by the following literature references which are specifically incorporated herein by reference. These biological effects include (1) facilitated memory and behavior, as reported by Beckwith, B. E. and Sandman, C. A., Neurosci. Biobehav. Rev., 2, 311-338 (1978); Handelmann, G. E., O'Donohue, T. L., Forrester, D. and Cook, W., Peptides, 4, 145-148 (1983) and de Kloet, R., and de Weid, D., Neuroendocrinol., 6, 157-199 (1960); (2) active avoidance behavior, as reported by Van Nispen, J. W. and Greven, H. M., Pharmac. Ther., 16, 67-102 (1982); (3) fetal growth and development, as reported by Swaab, D. G. and Martin, J. T., Peptides of the par intermedia, Ciba Foundation Symposium 81, Evered, D. and Lawrenson, G., eds., Pitman Medicals, London, 363-368 (1981); (4) adipose tissue lipolysis, as reported by Ramachandran, J., Farmer, S. W., Liles, S. and Li, C. H., Biochem. Biophys. Acta, 428, 347-354 (1976); (5) thermoregulation, as reported by Clark, W. G. and Lipton, J. M., Pharmac. Ther., 22, 249-297 (1983); (6) enhanced attention or motivation and improved memory consolidation, as reported by Bohus, B., Pharmacol., 18, 113-122 (1979); Pigache, R. M. and Rigter, H., Frontiers of Hormone Research, van Wimersma Greidanus, T. B. and Rees, L. H., eds. Karger, Basel, Vol. 8, 193-207 (1981); and (7) adrenal activity, as reported by Vinson, G. P., Whitehouse, B. J., Bell, A., Etinenne, E., Morris, H. R., Nature, 284, 464-467 (1980).

SUMMARY OF THE INVENTION

The present invention provides novel compounds which are cyclic analogs of α-melanotropin. The compounds are a series of cyclic, conformationally constrained analogs of α-melanotropin which display essentially no activity for the peripheral system receptors but which selectively display potent central nervous system activity.

The novel compounds may be used to induce a variety of physiological effects, including inter alia, facilitating memory and behavior, improving fetal growth and development, enhancing attention, improving socialization, stimulating sexual activity, reversing morphine analgesia and acting as an antidepressant.

In accordance with the present invention, there are provided polypeptides of the formula:

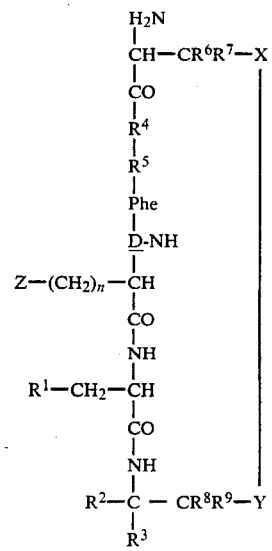

wherein
- $R^1$ is a substituted or unsubstituted aromatic radical;
- $R^2$ is hydrogen or a methyl group;
- $R^3$ is a carboxylate, carboxamide, hydroxymethyl, or aldehyde group or a peptide residue;
- $R^4$ is a simple amino acid residue;
- $R^5$ is a simple amino acid residue;
- $R^6$ and $R^7$, which may be the same or different, are hydrogen, methyl or lower alkyl having one to five carbon atoms;
- $R^8$ and $R^9$, which may be the same or different, are hydrogen, methyl or lower alkyl having one to five carbon atoms;
- X and Y are sulfur, methylene, SO or $SO_2$; Z is $-NH_2$,

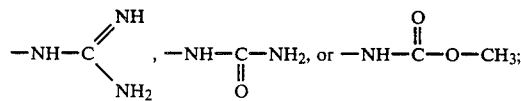

and
n is an integer greater than or equal to 2.

A preferred group of compounds within the present invention are cyclic α-melanotropin analogs having selective CNS activity of the formula:

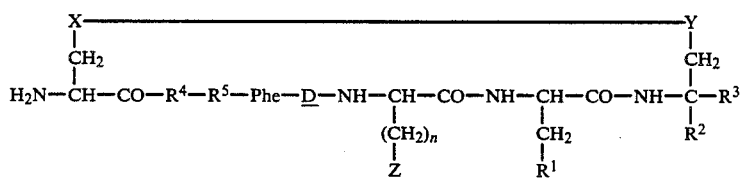

wherein
- $R^1$ is phenyl, indole, p-hydroxyphenyl, p-aminophenyl, imidazole, 1-naphthyl, 2-naphthyl or adamantyl;
- $R^2$ is hydrogen or a methyl group;
- $R^3$ is a carboxylate, carboxamide, hydroxymethyl, or aldehyde group or a peptide residue;
- $R^4$ is glutamic acid, alanine, α-amino butyric acid, valine, leucine or isoleucine;

- $R^5$ is histidine, glutamic acid, alanine, valine, leucine or isoleucine;
- X and Y are sulfur, methylene, SO, or $SO_2$;
- Z is $-NH_2$,

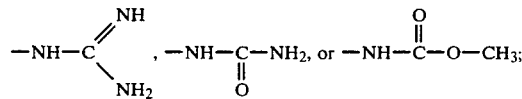

and
n is an integer greater than or equal to 2.
Particularly preferred compounds include:

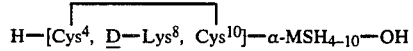

wherein $R^1$ is indole, $R^2$ is hydrogen, $R^3$ is COOH, $R^4$ is glutamic acid, $R^5$ is histidine, X and Y are sulfur, Z is $-NH_2$ and n is 4 and

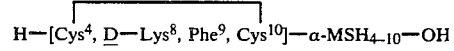

wherein $R^1$ is phenyl, $R^2$ is hydrogen, $R^3$ is COOH, $R^4$ is glutamic acid and $R^5$ is histidine.

Additional objects and advantages of the invention will be set forth in part in the description which follows, and in part will be obvious from the description, or may be learned from the practice of the invention. The objects and advantages may be realized and attained by means of the instrumentalities and combinations particularly pointed out in the appended claims.

DESCRIPTION OF THE PREFERRED EMBODIMENTS

Reference will now be made in detail to the presently preferred embodiments of the invention, which together with the following examples, serve to explain the principles of the invention.

As noted above, the present invention relates to polypeptides of the formula:

$$\begin{array}{c}
H_2N \\
| \\
CH-CR^6R^7-X \\
| \\
CO \\
| \\
R^4 \\
| \\
R^5 \\
| \\
Phe \\
| \\
\underline{D}\text{-NH} \\
Z-(CH_2)_n-CH \\
| \\
CO \\
| \\
NH \\
| \\
R^1-CH_2-CH \\
| \\
CO \\
| \\
NH \\
| \\
R^2-C-CR^8R^9-Y \\
| \\
R^3
\end{array}$$

wherein $R^1$ is a substituted or unsubstituted aromatic radical;
$R^2$ is hydrogen or a methyl group;
$R^3$ is a carboxylate, carboxamide, hydroxymethyl, or aldehyde group or a peptide residue;
$R^4$ is a simple amino acid residue;
$R^5$ is a simple amino acid residue;
$R^6$ and $R^7$ which may be the same or different are hydrogen, methyl or lower alkyl having one to five carbon atoms;
$R^8$ and $R^9$ which may be the same or different are hydrogen methyl or lower alkyl having one to five carbon atoms;
X and Y are sulfur, methylene, SO, or $SO_2$;
Z is $-NH_2$, $$-NH-C{\nearrow NH \atop \searrow NH_2}, \quad -NH-\underset{\underset{O}{\|}}{C}-NH_2, \text{ or } -NH-\underset{\underset{O}{\|}}{C}-O-CH_3;$$

and n is an integer greater than or equal to 2.

All amino acids are of the L configuration except for that in the 8-position, which is of the D configuration, and that in the 10-position, which can be either the D or L configuration.

As noted above $R^1$ may be either an unsubstituted or substituted aromatic radical. This term includes, inter alia, unsubstituted phenyl, 1 or 2-naphthyl, adamantyl, indole, and imidazole radicals or phenyl radicals substituted with nitro, amino, hydroxyl, halogen, methoxy, or small alkyl group or groups or the like.

When $R^6$ and $R^7$ are both methyl groups or when $R^8$ and $R^9$ are both methyl groups the amino acid residue in the four position is Penicillamine, "Pen." When an alkyl group or groups are in these positions the molecule is further restrained.

As noted above, a preferred group of compounds within the present invention are cyclic melanotropin compounds having central nervous system activity of the formula:

$$\begin{array}{c}
S\text{---------------------------------}S \\
| \qquad\qquad\qquad\qquad\qquad\qquad\qquad\qquad\qquad\qquad\qquad | \\
CH_2 \qquad\qquad\qquad\qquad\qquad\qquad\qquad\qquad\qquad\qquad CH_2 \\
| \qquad\qquad\qquad\qquad\qquad\qquad\qquad\qquad\qquad\qquad\qquad | \\
H_2N-CH-CO-Glu-His-Phe-\underline{D}-NH-CH-CO-NH-CH-CO-NH-C-R_3 \\
\qquad\qquad\qquad\qquad\qquad\qquad\qquad\qquad\qquad | \qquad\qquad | \qquad\qquad | \\
\qquad\qquad\qquad\qquad\qquad\qquad\qquad\qquad (CH_2)_n \qquad CH_2 \qquad R^2 \\
\qquad\qquad\qquad\qquad\qquad\qquad\qquad\qquad\qquad | \qquad\qquad | \\
\qquad\qquad\qquad\qquad\qquad\qquad\qquad\qquad\qquad Z \qquad\qquad R^1
\end{array}$$

wherein $R^1$ is phenyl, indole, p-hydroxyphenyl, p-aminophenyl, imidazole, 1-naphthyl, 2-naphthyl;
$R^2$ is hydrogen or a methyl group;
$R^3$ is a carboxylate, carboxamide, hydroxymethyl, or aldehyde group or a peptide residue;
Z is $-NH_2$, $$-NH-C{\nearrow NH \atop \searrow NH_2}, \quad -NH-\underset{\underset{O}{\|}}{C}-NH_2, \text{ or } -NH-\underset{\underset{O}{\|}}{C}-O-CH_3;$$

and n is an integer greater than or equal to 2.

Particularly preferred compounds include $H-[\overline{Cys^4,\underline{D}-Lys^8,Cys^{10}}]-\alpha\text{-MSH}_{4-10}-OH$, $H-[\overline{Cys^4,\underline{D}-Lys^8,Phe^9,Cys^{10}}]-\alpha\text{-MSH}_{4-10}-OH$, $H-[\overline{Cys^4,\underline{D}-Arg^8,Phe^9,D-Cys^{10}}]-\alpha\text{-MSH}_{4-10}-OH$, $H-[\overline{Cys^4,\underline{D}-Lys^8,Phe^9,D-Cys^{10}}]-\alpha\text{-MSH}_{4-10}-OH$, and $H-[\overline{Cys^4,\underline{D}-Arg^8,Trp^9,Cys^{10}}]-\alpha\text{-MSH}_{4-10}-OH$.

Specifically, the polypeptides of the present invention are cyclized analogs of α-melanotropin which exhibit a high degree of activity for the central nervous system and at the same time exhibit little or no peripheral activity. This increased CNS specificity is believed to be due in part to the increased structural rigidity of the claimed compounds. More specifically, the substantial CNS activity and minimal peripheral activity is believed to be attributed to the presence of a D-amino acid in the eight position, an L or D amino acid in the 10 position, the cyclic portion of the compound and an aromatic radical in the 9 position. The conformation and structure of the compounds of the present invention appears to be that required for activity at the CNS receptors, but appears to exclude substantially the conformation and structure required for activity at the peripheral receptors. Extensive studies have been conducted which examine these structure/conformation relationships. See generally, Hruby, V. J., "Perspectives in Peptide Chemistry," Eberle, A., Geiger, R, and Wieland, T., eds., S. Karger, Basel, Switzerland, 207-220 (1981); Hruby, V. J., "Topics in Molecular Pharmacology," Burgen, A. S. V. and Roberts, G. C. K., eds., Elsevier/North Holland Biomedical Press, Amsterdam, 99-126 (1981); Hruby, V. J. and Mosberg, H. I., "Hormone Antagonists," M. K. Agarwal, ed., Walter De Gruyter & Co., Berlin, 433-474 (1982); Hruby, V. J., Life Sciences, 31, 189-199 (1982); Hruby, V. J., Mosberg, H. I, Sawyer, T. K., Knittel, Rockway, T. W., Ormberg, Jr, Darman, P., Chan, W. Y., and Hadley, M. E., Biopolymers, 22, 517-530 (1983); and Hruby, V. J., "Conformationally Directed Drug Design, Peptides and Nucleic Acids as Templates or Targets," Vida, J. A. and Gordon, M., eds., ACS Monograph Series 251, Washington, D.C., 9-27 (1984), which are specifically incorporated by reference herein.

One of the unique features of some of the preferred α-MSH analogs of the present invention is the incorporation of a cysteine amino acid residue in the 4 position and either the L or D-cysteine amino acid residue in the 10 position of the α-MSH$_{4-10}$. A basic D-amino acid residue is incorporated into the eight position and an aromatic amino acid residue is incorporated into the nine position of the α-MSH$_{4-10}$ sequence. for example, a preferred polypeptide showing increased CNS activity and minimal peripheral activity is

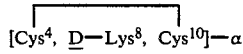

—MSH$_{4-10}$—OH and has the following formula:

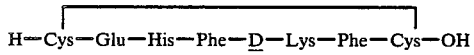

All compounds are cyclic and it is believed that the conformational and structural constraints this imposes accounts in part for the unique biological activities. The compounds are believed to induce a variety of pharmacological manifestations such as reversal of morphine analgesia, tolerance and dependence, enhancement of memory, enhancement of fetal growth, improvement of mood and attention, improved socialization, and stimulation of sexual activity. The compounds may also be used as antidepressants. In addition, the compounds of the present invention act as antipyretics and act in centrally directing effects on visceral function such as blood pressure regulation, bladder control and thermoregulation. See generally, Murphy, M. T., Richards, D. B., and Lipton, T. M., Science: 221, 192-193 (1983) Contreras, P. C. and Takemori, A. E., J. Pharmacol. Exp. Ther.: 229, 21-26 (1984) which are specifically incorporated by reference herein.

As previously stated the compounds of the present invention exhibit exceptional CNS activity while exhibiting minimal peripheral activity. Central nervous system activity is determined in an assay which measures the ability of peptides to reverse or inhibit the in vivo analgesia induced in rats by morphine compared to the ability of the peptide to cause skin darkening in frogs in vivo. For a discussion of these assays see generally, Beckwith, B. E. and Sandman, C. A., Peptides, 3, 411-420 (1982) and Zimmerman, E. and Krivoy, W. A., Prog. Brain Res.; 39, 383-394 (1973), which are specifically incorporated by reference herein.

The compounds of the present invention were tested for their relative activity in the frog skin bioassay system and in the rat tail flick assay and the hot plate assay. Compounds of the present invention showed increased CNS activity with minimum peripheral activity. Table I illustrates the CNS specificity for some of the compounds of the present invention. As Table I demonstrates both

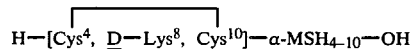

and

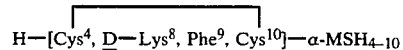

have substantially more CNS activity than α-MSH and the compounds have less than 1/10,000 to 1/300,000 the peripheral activity of α-MSH. When the compounds of the present invention were administered to the rats compulsive mutual grooming behavior was observed.

Preparation of compounds within the scope of the present invention appear in the following examples.

EXAMPLE I

Preparation of Nα-tert-butyloxycarbonyl-S-p-methylbenzyl-L-cysteinyl-O-γ-benzyl-L-glutamyl-N$^{im}$-tosyl-L-histidyl-L-phenylalanyl-N$^ε$-benzyloxycarbonyl-D-lysyl-L-phenylalanyl-S-p-methylbenzyl-L-cysteinyl-resin.

Chloromethylated (1.1 mmoles Cl/g resin) polystyrene resin crosslinked with 1% divinylbenzene was used as the solid phase matrix. The carboxyl terminal amino acid N$^α$-Boc-L-Cys(Bzl) was attached via an ester linkage to the resin to a substitution level of 0.39 mmoles of the protected amino acid/g resin. Then 10.5 g of the above dry Boc-L-Cys(Bzl)-resin was placed into a solid phase peptide synthesis reaction vessel and Boc-Phe, Boc-D-Lys(N$^ε$-Cbz), Boc-Phe, Boc-His(N$^{im}$-Tos), Boc-Glu-(γ-O-Bzl), and Boc-Cys(S-p-MeBzl) were then incorporated onto the peptide resin sequentially according to the protocol listed in Agenda A.

Agenda A

1. Wash for 2 min. with CH$_2$Cl$_2$ (repeat this step 4 times).
2. Treat with 45% trifluoroacetic acid (hereinafter TFA) in CH$_2$Cl$_2$ containing 2% anisole (v/v) for 5 min.
3. Treat as in #2 for 25 min.
4. Wash for 2 min. with CH$_2$Cl$_2$ (repeat 3 times).
5. Wash for 2 min. with MeOH (repeat 3 times).
6. Wash for 2 min. with CH$_2$Cl$_2$ (repeat 3 times).
7. Treat with 10% triethylamine (hereinafter TEA) in CH$_2$Cl$_2$ (v/v) for 5 min. (repeat 2 times).
8. Wash for 2 min. with CH$_2$Cl$_2$ (repeat 4 times).
9. Ninhydrin test—Kaiser et al., Anal. Biochem., 34, 595 (1970), which is herein specifically incorporated by reference. If positive, proceed to step 10; if negative repeat steps 2-9.
10. Treat with 3.5 equivalents of the appropriate Boc amino acid derivative dissolved in CH$_2$Cl$_2$ or dimethylformamide (hereinafter DMF) and 3.2 equivalents each of dicyclohexylcarbodiimide (hereinafter DCC) in CH₂Cl₂, and 1-hydroxybenzotriazole (hereinafter HOBT) in DMF/CH₂Cl₂. Allow reaction to proceed for 10 min. to overnight.

11. Wash for 2 min. with CH₂Cl₂ (repeat 3 times).
12. Wash for 2 min. with MeOH (repeat 3 times).
13. Wash for 2 min. with CH₂Cl₂ (repeat 4 times).
14. Ninhydrin test—If coupling is incomplete, repeat steps 10–14.

There was obtained 14.88 g of the title compound.

EXAMPLE II

Preparation of L-cysteinyl-L-glutaminyl-L-histidyl-L-phenyl-alanyl-D-lysyl-L-phenylalanyl-L-cysteinyl-cyclic (4-10) disulfide.

14.88 g of the protected peptide resin from Example I was reacted with 110 ml of anhydrous HF and 30 ml of anisole at 0° C. for 1 hr. The mixture was evaporated in vacuo and the dried mixture of free peptide and resin was washed several times with anhydrous ethyl ether which was then discarded. The peptide resin mixture was then extracted with 50% aqueous acetic acid, then with glacial acetic acid and finally with deionized water, all under nitrogen. All of the acetic acid and aqueous extractions were combined and the solution was lyophilized to give 2.64 g of a powder. This powder was dissolved in 3 liters of 0.1N degassed aqueous ammonium acetate and the pH adjusted to 8.2. The sulfhydryl oxidation was done by slow addition of 1 liter of 0.01N K₃Fe(CN)₆ solution. The oxidation was allowed to proceed for an additional 1–2 hrs. and then the pH was lowered to 5 with the addition of glacial acetic acid. The ferro-and excess ferricyanide was removed by the addition of Rexyn AG3-X4-A anion exchange resin and the mixture was stirred for 90 min. The resin was filtered off, washed three times with 30% aqueous acetic acid, and the solution lyophilized to give a cream colored powder. The powder was dissolved in 10% aqueous acetic acid, filtered through a millipore filter and placed on a Sephadex G-25 column (5×100 cm) which had been previously equilibrated with 10% acetic acid. The product was eluted with 10% HOAc and the tubes containing peptide material combined and lyophilized to give 1.53 g of powder. The compound was further purified by ion exchange on carboxymethylcellulose (hereinafter CMC). The peptide was dissolved in 0.01M ammonium acetate, filtered through a millipore filter, and then loaded on the CMC column. The column was first eluted with 0.01M ammonium acetate having a pH of 4.5, then with 0.05M ammonium acetate having a pH of 6.8, and finally with 0.1M ammonium acetate. The product was further purified by gel chromatography on Sephadex G-15 using 2% acetic acid as the eluent solvent. The yield was 103 mg of pure title compound.

Amino Acid Analysis: Glu 1.04; half-Cys 1.86; Phe 2.00; His 1.02; Lys 1.00.

HPLC Analysis: Beckman G8 5μ Ultrasphere, 4.6 mm×25 cm at flow rate of 1–2 ml/min; solvent gradient of A=0.25M triethylammonium phosphate pH 3.2 and B=CH₃OH from 20–75% B in 25 min.; product elutes at 9.23 minutes.

TLC Analysis: Rf=0.48 (BAWE); 0.19 (BAW); 0.03 (BAW upper); 0.56 (BAWP); as used above, the following abbreviations for solvent systems have the following connotations: BAWE refers to 1-butanol; acetic acid, water, EtOAc (1:1:1:1)v/v/v/v/; BAW refers to 1-butanol, acetic acid, water, (45:5:12.5); BAWP refers to 1-butanol, acetic acid, water, pyridine (30:6:24:20);

BAW-upper refers to 1-butanol, acetic acid, water (4:1:5), upper phase only.

EXAMPLE III

Preparation of L-Cysteinyl-L-glutaminyl-L-histidyl-L phenylalanyl-D-arginyl-L-phenylalanyl-D-cysteinyl-cyclic (4-10) disulfide.

The procedure in Example I was followed except that 10.48 g of Nα-Boc-S-p-methylbenzyl-D-cysteinyl resin with a substitution 0.35 mmol of amino acid per gram of resin was used (3.67 mmol). Then Boc-Phe, Boc-D-Arg(N$^G$-Tos), Boc-Phe, Boc-His(N$^{im}$-Tos), Boc-Glu(γ-O-Bzl); and Boc-Cys(S-p-MeBzl) were added as outlined in Agenda A. There was obtained 13.98 g of Boc-Cys(S-p-MeBzl)-Glu(γ-OBzl)-His(N$^{im}$-Tos)-Phe-D-Arg(N$^G$-Tos)-Phe-Cys(S-p-MeBzl)-resin.

The peptide resin was treated as in Example II with liquid HF containing anisole to obtain 2.32 g of crude peptide material. Following oxidation with aqueous K₃Fe(CN)₆ at pH 8.4 as described in Example II, the compound was purified first by gel filtration on Sephadex G-25 using 10% aqueous acetic acid as the eluent solvent, then by CMC ion exchange chromatography using successively 0.05N NH₄OAc, pH 6.8 and then 0.1N NH₄OAc, pH 6.9 as eluent solvents (the product came out with the pH 6.9 buffer) and finally by gel filtration on G-25 using 2% aqueous acetic acid as the eluent solvent. There was obtained 318 mg (9.2%) of the title compound.

Amino Acid Analysis: Glu, 1.09; half-Cys, 2.00; Phe, 1.87; His, 0.96; Arg, 0.98.

HPLC Analysis: Same conditions as Example II; product elutes at 8.95 minutes.

TLC Analysis: Rf 0.70 (BAWP); 0.22 (BAW-upper); 0.65 (BAWE), same as in Example II.

EXAMPLE IV

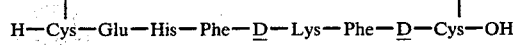

cyclic (4-10) disulfide.

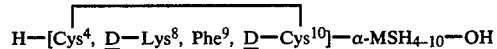

was prepared as in Examples I and II.

EXAMPLE V

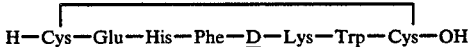

cyclic (4-10) disulfide was prepared as in Examples I and II but without ion exchange chromatography and with HF cleavage using ethanedithiol.

EXAMPLE VI

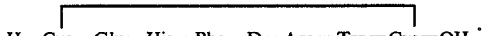

cyclic (4-10) disulfide was prepared as in Examples I and II using the full complement of purification methods and with HF cleavage using 10% ethanedithiol in the cleavage mixture.

The assays are described in detail below.

In Vivo Bioassays. Morphine antagonism was tested in Sprague-Dawley rats (250-300 g) by administering the compounds of the present invention and measuring the latency to rear paw lick and jumping.

Each rat received either a water vehicle or an α-MSH analog intraperitoneally. Thirty minutes later 5 mg/kg of morphine was administered to all animals and 30 minutes after the administration of the morphine, the percent analgesia was measured. Each animal was placed on a 55° C. hot plate. A sixty second cut-off was used and animals not responding within this time was considered analgesic. The results of these tests are summarized in Table I. Percent analgesia was calculated as follows:

$$100 \times \frac{\text{test latency} - \text{control latency}}{60 \text{ sec} - \text{control latency}}$$

Antagonism to morphine analgesia was also measured using the tail flick test. The tails of the treated animals were placed in a 55° C. water bath and the latency of the animals to withdraw was measured in seconds. A fifteen second cut-off time was used.

Percent analgesia in the tail flick test was calculated as follows:

$$100 \times \frac{\text{test latency} - \text{control latency}}{15 - \text{control latency}}$$

The peripheral activity of the compounds was tested using the frog skin bioassay system. See O'Donohue, T. L. and Dorsa, D. M., Peptides, 3, 353-395 (1982) and Hadley, M.E. et. al., Science, 213, 1025-1027 (1981) which are herein specifically incorporated by reference. Peptides were injected into the dorsal lymph sac of the frog Rana pipiens in amounts up to 20 mg. Skin coloration was observed for 30 minutes. The lowest dose of peptide that produced skin darkening within the 30 minute observation period was determined. For example, in Table I, only 0.1 ng/g of α-MSH was administered before skin darkening was observed. In contract, 30 μg/g of

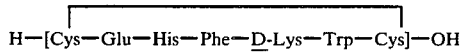

was administered and no skin darkening was observed.

TABLE I

| Structure | Biological Activities of α-Melanotropin Analogs | | Minimum dose Producing Skin Darkening |
|---|---|---|---|
| | Percent Analgesia[b] | | |
| | Tail Flick | Hot Plate | |
| H—[Cys—Glu—His—Phe—D-Arg—Phe—D-Cys]—OH[a] | 34.3 | 42.6 | >1 μg/g |
| H—[Cys—Glu—His—Phe—D-Lys—Phe—Cys]—OH[a] | 14.9 | 15.5 | >1 μg/g |
| H—[Cys—Glu—His—Phe—D-Lys—Phe—D-Cys]—OH[a] | 10.5 | 15.0 | 1 μg/g |
| H—[Cys—Glu—His—Phe—D-Lys—Trp—Cys]—OH[a] | 1.5 | N.T.[c] | >30 μg/g |
| H—[Cys—Glu—His—Phe—D-Arg—Trp—Cys]—OH[a] | 6.7 | N.T.[c] | >20 μg/g |
| α-MSH | 18.6 | N.T.[c] | 0.1 ng/g |
| β-MSH | 11.9 | 26.9 | N.T.[c] |
| Water (vehicle) control | 48.9 | 56.1 | N.T.[c] |

[a] All compounds showed "compulsive mutual grooming" activity in rats.
[b] Reversal of morphine analgesia, 100 μg peptide given I.P.
[c] N.T. = not tested.

It will be apparent to those skilled in the art that various modifications and variations can be made in the processes and products of the present invention. Thus, it is intended that the present invention cover the modifications and variations of this invention provided that they come within the scope of the appended claims and their equivalents.

What is claimed is:

1. A polypeptide which is a cyclic analog of α-MSH and has the formula:

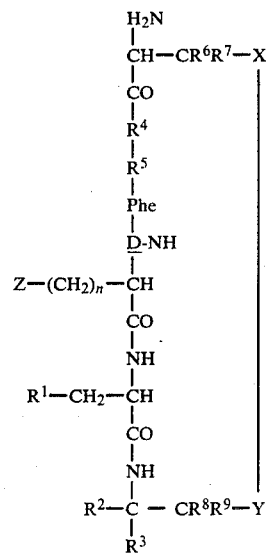

wherein
- R¹ is a substituted or unsubstituted aromatic radical;
- R² is hydrogen or a methyl group;
- R³ is a carboxylate, carboxamide, hydroxymethyl, or aldehyde group;
- R⁴ is glutamic acid, alanine, -amino butyric acid, valine, leucine or isoleucine;
- R⁵ is histidine, glutamic acid, alanine, valine, leucine or isoleucinei;
- R⁶ and R⁷, which may be the same or different, are hydrogen, methyl or lower alkyl having one to five carbon atoms;
- R⁸ and R⁹, which may be the same or different, are hydrogen, methyl or lower alkyl having one to five carbon atoms;
- X and Y are sulfur, methylene, SO, or SO₂;
- Z is —NH₂,

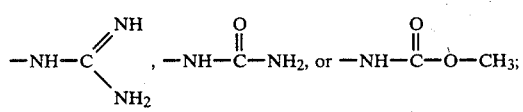

and
n is an integer greater than or equal to 2.

2. A cyclized melanotropin compound comprising:

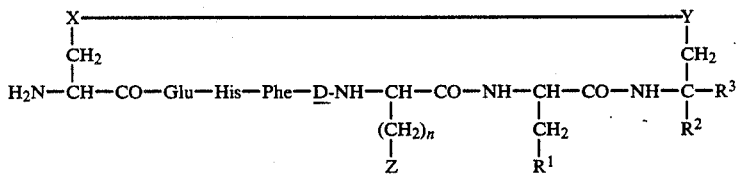

wherein
- R¹ is phenyl, indole, p-hydroxyphenyl, p-aminophenyl, imidazole, 1-naphthyl adamantyl or alkylphenyl, 2-naphthyl;
- R² is hydrogen or a methyl group;
- R³ is a carboxylate, carboxamide, hydroxymethyl, or aldehyde group;
- X and Y are sulfur, methylene, SO, or SO₂;
- Z is —NH₂,

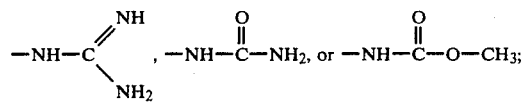

and
n is an integer greater than or equal to 2; and wherein said cyclized portion of said compound is conformationally restricted in a manner which is compatible with the reactivity of said compound with receptors of the central nervous system.

3. A polypeptide according to claim 1 having the formula:

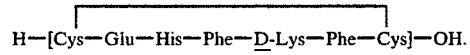

4. A polypeptide according to claim 1 having the formula:

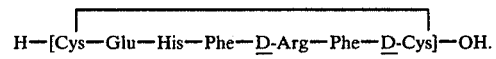

5. A polypeptide according to claim 1 having the formula:

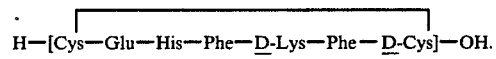

6. A polypeptide according to claim 1 having the formula:

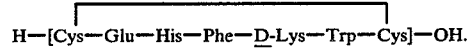

7. A polypeptide according to claim 1 having the formula:

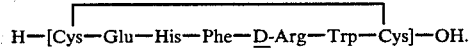

8. A compound according to claim 2, having the formula:

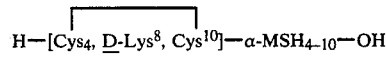

wherein
- R¹ is an indole group;
- R² is hydrogen;
- R³ is —COOH;

X and Y are each sulfur;
Z is —NH₂; and
n=4.

9. A compound according to claim 2 having the formula:

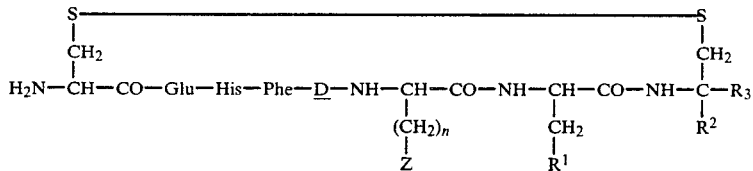

wherein
R¹ is phenyl, indole, p-hydroxyphenyl, p-aminophenyl, imidazole, 1-naphthyl, 2-naphthyl or alkylphenyl;
R² is hydrogen or a methyl group;
R³ is a carboxylate, carboxamide, hydroxymethyl, or aldehyde group;
Z is —NH₂,

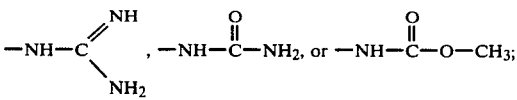

and
n is an integer greater than or equal to 2.

10. A compound according to claim 2 wherein the compound is an antidepressant.

11. A compound according to claim 2 wherein the compound is an antipyretic.

12. A compound according to claim 2 wherein the compound reverses morphine analgesia in humans and lower animals; is an antidepressant; improves socialization in humans and lower animals; improves memory, attention or mood in humans and lower animals; stimulates sexual activity in humans and lower animals; or is an antipyretic.

* * * * *